US006814490B1

(12) United States Patent
Suhm et al.

(10) Patent No.: US 6,814,490 B1
(45) Date of Patent: Nov. 9, 2004

(54) DEVICE FOR MOVING A MEDICAL APPARATUS IN A CONTROLLED MANNER

(75) Inventors: Norbert Suhm, Wil-Haltingen (DE); Peter Messmer, Oberwil (CH); Pietro Regazzoni, Basel (CH); Paul Müller, Riehen (CH); Urs Bopp, Basel (CH); Markus Hehli, Frauenkirch (CH); Silvio Koller, Davos-Dorf (CH)

(73) Assignee: AO-Entwicklungsinstitut Davos, Davos (CH)

( * ) Notice: Subject to any disclaimer, the term of this patent is extended or adjusted under 35 U.S.C. 154(b) by 0 days.

(21) Appl. No.: 10/181,115
(22) PCT Filed: Jan. 14, 2000
(86) PCT No.: PCT/CH00/00022
§ 371 (c)(1),
(2), (4) Date: Sep. 23, 2002
(87) PCT Pub. No.: WO01/50959
PCT Pub. Date: Feb. 19, 2001

(51) Int. Cl.$^7$ .................................................. H05G 1/02
(52) U.S. Cl. ....................................... 378/198; 378/195
(58) Field of Search ................................. 378/195–198

(56) References Cited

U.S. PATENT DOCUMENTS

| 4,341,279 | A |   | 7/1982  | Waerve            |        |
|-----------|---|---|---------|-------------------|--------|
| 4,589,126 | A |   | 5/1986  | Augustsson et al. |        |
| 4,697,661 | A |   | 10/1987 | Pajerski et al.   |        |
| 4,935,949 | A |   | 6/1990  | Fujita et al.     |        |
| 5,638,420 | A | * | 6/1997  | Armistead         | 378/57 |
| 5,762,608 | A |   | 6/1998  | Warne et al.      |        |
| 6,120,180 | A |   | 9/2000  | Graumann          |        |

FOREIGN PATENT DOCUMENTS

DE  197 01 346 A1  7/1998

OTHER PUBLICATIONS

Patent Abstracts of Japan, Patent Number JP8229028, Publication Date: Sep. 10, 1996, X–RayDiagnostic Device.
Patent Abstracts of Japan, Patent Number JP11188027, Publication Date: Jul. 13, 1999, Medical Diagnosis Device.
WO 98/19875, Publication Date: May 14, 1998, A Modular Wheel Assembly.
WO 00/32462, Publication Date Jun. 8, 2000, A Modular wheel and/or Conventional Wheel Assembly and Control System.

* cited by examiner

Primary Examiner—Craig E. Church
(74) Attorney, Agent, or Firm—Rankin, Hill, Porter & Clark LLP

(57) ABSTRACT

A device for moving an X-ray apparatus embodied in the form of a C-bow (9) in a controlled manner, the C-bow (9) being mounted on a pedestal (31) provided with motor-driven rollers (3) controllable in their direction of travel in such a way that it is displaceable in parallel in relation to at least two axes (18;19) and rotatable relative to three axes (18; 19, 21), each movement of the C-bow (9) with respect to a coordinate system (29) which is stationary relative to the room being carried out via controllable drive devices (6;7;37;38). These drive devices (6; 7; 37; 38) are controlled either by means of a control device (39;48) or via a computer (23), said control device being operated either via a sterile control console or by voice control. Any positions and projections of the C-bow (9) that have once been adjusted may be stored in the computer (23), so that a desired position and projection may be reproduced again. If the C-bow 9 is combined with a surgical navigation system which comprises a position detector (27), it is possible, by measuring a reference base that is applied to a patient (12) and is provided with optical markers (28), to consider changes in the position of the patient (12) in such a way that an adjusted position and projection of the C-bow (9) can be reproduced after the patient (12) has changed position.

29 Claims, 5 Drawing Sheets

DEVICE FOR MOVING A MEDICAL APPARATUS IN A CONTROLLED MANNER

The invention relates to a device for moving a medical apparatus in a controlled manner as claimed in the precharacterising part of claim 1 and to a method for moving a medical apparatus in a controlled manner as claimed in the precharacterising part of claim 25.

X-ray apparatuses, particularly those having a C-shaped bow provided with an X-ray source mounted on one end and an X-ray receiver mounted on the other end thereof (in the following briefly referred to as "C-bow") are part of the standard operating-theatre equipment in emergency surgery. Apparatuses of this type serve for intra-operative imaging purposes, making it possible to control the repositioning manoeuvres necessary for the treatment of bone fractures and to monitor the insertion of implants stabilising the fracture. When the C-bow is used in combination with modern surgical navigation systems, a continuous visualisation of the surgical procedure is made possible by means of fluoroscopic images which are created intra-operatively and may be stored in a computer.

As the procedure described above implies working with X-rays in the presence of persons, i.e. the patient and the operating-room staff, the positioning of the X-ray apparatus should be carried out in such a way as to avoid long periods of fluoroscopic exposure, in other words the exact position should be found right at the first attempt. However, according to the usual practice, the C-bow in the operating theatre is not moved by the operating surgeon him-/herself but by a member of the operating-room staff. The mere communication between the operating surgeon and said member of the operating-room staff concerning the execution of a specific movement of the apparatus relative to the patient may give rise to numerous errors. Often, the C-bow is used after an individual step of an operative procedure in order to control and document the success of the intervention. If a correction of the provisional result of an intervention is necessary, the C-bow must be removed again from the right position which had just been found with difficulty, as the apparatus would otherwise be in the way of the operating surgeon performing the correction on the implant or on the fracture site. In order to perform the control which is subsequently necessary, the C-bow must be brought into the "right" position again, which had already been determined before. This may often lead to long periods of exposure before the image intensifier will generate the right image. A C-bow provided with a "memory" for positions which have once been correctly adjusted would represent a considerable improvement.

A drive device for different vehicles comprising modular, motor driven and controllable rollers is known from WO 98/19875 GRANT. The drive device is controllable by means of a computer having wireless access e.g. to road maps or positioning systems.

A medical system provided with rollers is known from DE 197 01 346 SIEMENS. This known medical system is provided with controlling means for the rollers realized by means of rails and comprises a remote control unit.

Another medical device having motor driven and controllable rollers is known from U.S. Pat. No. 4,589,126 AUGUSTSSON. The control of the drive devices is realized in one embodiment of this known device by means of a computer.

Disadvantageous at these known device is that the computer serving for the control of the drive devices has to be programmed before the treatment or has to be fed with control instructions through an external "fix" positioning system.

The invention is intended to provide a remedy for this. It is accordingly an object of the invention to create a device for moving a medical apparatus, particularly an X-ray apparatus, in a controlled manner.

According to the invention, this object is achieved by means of a device for moving a medical apparatus, particularly an X-ray apparatus, in a controlled manner which shows the features of claim 1, and by a method for moving a medical apparatus in a controlled manner which shows the features of claim 25.

Variant without Surgical Navigation System (Basis Version)

The advantage achieved by this consists in the fact that here the X-ray apparatus is moved by the operating surgeon him-/herself. There is no need any more for a second person interpreting and executing the instructions of the operating surgeon which the latter has encoded in his own coordinate system.

The inventive device for moving a medical apparatus in a controlled manner enables a controllable positioning of an apparatus, in particular an X-ray apparatus, in the two dimensions (x/y) of a plane, especially a plane extending parallel to the floor of the operating theatre. The device comprises at least three motor-driven rollers provided with a first axis of rotation extending parallel to said plane and intersecting the centre of the roller, and a second axis of rotation extending perpendicularly to said plane and lying in the plane of the roller or parallel thereto. The rollers are fixedly positioned relative to each other. Each of the rollers is provided with a first drive device by means of which the roller may be rotated about the first axis of rotation and with a second drive device by means of which the roller may be rotated about the second axis of rotation in order to change its direction of travel.

The rollers may be fixed either directly on the medical apparatus via their second axes of rotation or may be fixed, via their second axes of rotation, on a frame serving as a platform for the medical apparatus. The version with a platform is particularly suitable for retrofitting existing apparatuses, whereas the version with the rollers fixed directly on the apparatus will rather be taken into consideration for new apparatuses.

Stepper motors, in particular electronically controllable stepper motors, may be used as first and second drive devices. Stepper motors based on digital drive technology are equally possible. Further details concerning stepper motors of this type may be found, for example, in Dubbel; Taschenbuch für den Maschinenbau (Pocket Book of Mechanical Engineering); Eds. W. Beitz and K.-H. Grote; Springer Verlag, 19th edition, 1997; Pages: T9 and V29.

The X-ray apparatus according to the invention is preferably realised in the form of a C-bow which is mounted on the inventive device by means of a pedestal. C-bows are usually provided, in addition to the two directions of displacement defined by the plane extending parallel to the floor of the operating theatre, with further axes of motion permitting a movement of the C-bow relative to the displaceable pedestal, which merely serves for displacing the apparatus parallel to the floor. For the handling of the C-bow, at least one linear movement of the C-bow parallel to an axis extending vertically to the floor of the operating theatre (z-axis) as well as motions of rotation about at least two further axes are necessary.

These movements of the C-bow are equally performed in a motor-driven manner. The drive devices for these motions may equally be stepper motors, as described above for the rollers of the inventive device. Linear movements are suitably performed by linear motors such as those described in detail in Dubbel; Taschenbuch für den Maschinenbau (Pocket Book of Mechanical Engineering); Eds. W. Beitz and K.-H. Grote; Springer Verlag, 19th edition, 1997; Pages: T9 and V31.

All the drives mentioned above may either be subject to the direct visual control of the operating surgeon or be controlled by retrieval of stored data relating to a previously occupied position or projection.

1. In this embodiment of the X-ray apparatus according to the invention, the initial positioning of the C-bow is carried out by the operating surgeon under direct visual control by either of the following means:
    a) by using a preferably wireless, sterilisable control console; or
    b) by voice control (e.g. using the following instructions: forward, backward, to the right, to the left, fast, slowly, turn about axis A,B,C).
2. For permitting a positioning of the C-bow by retrieval of stored data, the X-ray apparatus according to the invention comprises in addition a computer equipped with at least a data memory, a display screen, and a keyboard. In order to reproduce a previously occupied projection, it is thus possible with the aid of the computer to store the lengths and the temporal succession of the displacements performed during the initial positioning in the data memory and to reproduce them by activating a control function stored in the computer. The activation of the control function may in turn be performed either by means of the control console or by voice control (e.g. using the instructions: position 1, position 2).

The advantage achieved by the X-ray apparatus according to the invention consists in the fact that the positions and projections occupied by the C-bow are storable and can thus be automatically reproduced from any given position by the retrieval of the stored data. This is of advantage, for example, for monitoring tasks to be performed upon completion of corrective work done on an implant or a bone fracture in the course of which the C-bow has been removed from its position so as not to be in the way of the operating surgeon. The control device of the C-bow is thus provided with a "memory function" concerning previously adjusted projections. Positions and projections of the C-bow relative to the patient that have once been intra-operatively defined may, therefore, be reproduced after completion of further surgery any number of times without necessity of additional fluoroscopic controls to determine the right positioning. In addition, the computer-controlled embodiment permits to visualise the planned displacement of the C-bow on the display screen of the computer, which makes it possible to avoid collisions with objects present in the operating theatre that might otherwise occur during the automatic positioning of the C-bow.

C-bow with Combined Surgical Navigation System

In a further embodiment of the X-ray apparatus according to the invention, said X-ray apparatus is run in combination with a surgical navigation system. Such surgical navigation systems comprise at least one computer equipped with a data memory and with adequate operator's controls as well as a preferably optoelectronic position detector for detecting the position of optical markers in a three-dimensional coordinate system within the operating theatre. As a surgical navigation system, an apparatus called "Surgigate" may be used, which is put on the market by the company MEDIVISION, Oberdorf, Switzerland. Often, such navigation systems function in combination with an optoelectronic position detector, for example the commercially available apparatus Optotrak 3020 (three-dimensional motion measurement system) by Northern Digital, Ontario, Canada. The tasks of the computer controlling the drive devices of the C-bow may here be fulfilled by the computer that is integrated in the navigation system. For permitting the detection of the position and projection of the C-bow, said C-bow is provided with at least three non-collinear, optical markers, preferably LEDs (light emitting diodes) or IREDs (infrared light-emitting diodes). The positions of the optical markers within the three-dimensional coordinate system of the operating theatre is measured by the optoelectronic position detector and the coordinates thus obtained are stored in the data memory of the computer. From the positions of all markers, the position and projection of the C-bow in the operating theatre can be calculated by the computer.

In order to initially move the C-bow into a desired position, the system may be provided with an additional integrated control device (similarly to the embodiment without a combined surgical navigation system) intended for realising the first, or primary positioning of the C-bow.

This additional control device may optionally be realised by one of the following means:
    a) vocal control of the C-bow via voice input;
    b) control of the C-bow via a sterile control console (virtual keyboard) which may be integrated in the surgical navigation system; and
    c) control of the C-bow by means of a pointer provided with optical markers.

The pointer according to c) comprises at least three optical, non-collinear markers, preferably LEDs (light-emitting diodes) or IREDs (infrared light-emitting diodes), which are fixed on a rod. The pointer is oriented by the operating surgeon in such a way relative to the patient that the longitudinal axis of the rod simulates the central X-ray of the C-bow. In order to define the position and orientation of the pointer, the three-dimensional positions of the optical markers are measured by means of the measuring device and the position and orientation of the pointer is subsequently determined by the computer. The computer also permits to determine a plane within a three-dimensional space which extends perpendicularly to the longitudinal axis of the pointer. This plane defines the desired projection plane for the primary positioning of the C-bow. Subsequently, the X-ray apparatus is given the instruction to occupy the position and projection thus defined.

In the embodiment just described, the positions and projections occupied by the C-bow may equally be stored in the computer, which makes it possible, by a later retrieval of the corresponding data, to reproduce the positions and projections previously occupied by the C-bow.

The utilisation of a surgical navigation system with an integrated position detector offers in addition the possibility of applying a reference base to a patient's body which is provided with at least three non-collinear markers. Thus, it is possible to measure intra-operative changes in the position of the patient by measuring the positions of these markers and to store the modified position of the reference base in the data memory of the computer. Assuming that after the patient has been moved to a modified, second position within the operating theatre an X-ray photograph is to be taken the projection plane of which should correspond to that of an X-ray photograph taken previously while the patient had occupied the first position, it is possible, by means of the computer, to perform a coordinate transformation, calculating the position and projection of the C-bow and moving the C-bow into said position and projection which makes it possible, while the patient occupies the second position, to take an X-ray photograph in a projection plane corresponding to that of the X-ray photograph taken while the patient had occupied the first position. In this way, an identical image plane can be reproduced in spite of possible movements of the reference bases, which may occur, for example, during fracture reduction. In other words, this embodiment of the X-ray apparatus according to the invention allows for possible movements of the patient when reproducing stored projections.

For supervision purposes, it is desirable to have a possibility of reproducing the position and projection of the C-bow which is identical to a previously occupied position and projection. This may be realised by combining the computer with the additional control device of the C-bow mentioned above. As in the above example, the input of the control instructions for this additional control device may optionally be realised by one of the following means:

a) control of the C-bow via voice input;
b) control of the C-bow via a sterile control console (virtual keyboard) which may be integrated in the surgical navigation system; and
c) control of the C-bow by means of a pointer provided with optical markers.

The advantages achieved by the present invention consist essentially in the fact that the device according to the invention makes it possible to use the image intensifier in the emergency surgery operating theatre in the usual way while permitting it with the aid of the control device to occupy positions that will yield immediately the desired image plane and to reproduce these positions after completion of further surgery any number of times by retrieval of stored data.

The inventive method for moving a medical apparatus, particularly an X-ray apparatus, in a controlled manner by means of one of the devices described above comprises the following procedure steps:

A) input by the operator of an instruction to move the apparatus to a desired position;
B) transformation of this instruction into control signals by means of a control device;
C) transmission of these control signals to the drive devices mounted on the device;
D) displacement of the movable elements to the desired position by means of the drive devices.

The computer input of the instruction by the operator may be realised by means of a hand-operated control console, by voice control, or via a keyboard or a mouse.

The utilisation of a computer makes it possible to store any position occupied by the apparatus in the data memory of the computer, the position of the apparatus being calculable by the computer and storable in the data memory once the lengths and the temporal succession of the displacements of the movable elements have been determined.

If an optoelectronic position detector is used, said position, instead of being calculated, may also be determined by measuring the positions of optical markers fixed to the apparatus via the optoelectronic position detector and subsequently be stored in the data memory.

If the device is used in combination with a computer, it presents the advantage that a previously occupied position of the apparatus may be reproduced by activating a control function and retrieving the data stored in the data memory.

In the following, the invention and improvements of the invention will be illustrated in greater detail with reference to the partially diagrammatic representations of several embodiments.

Figure 1:
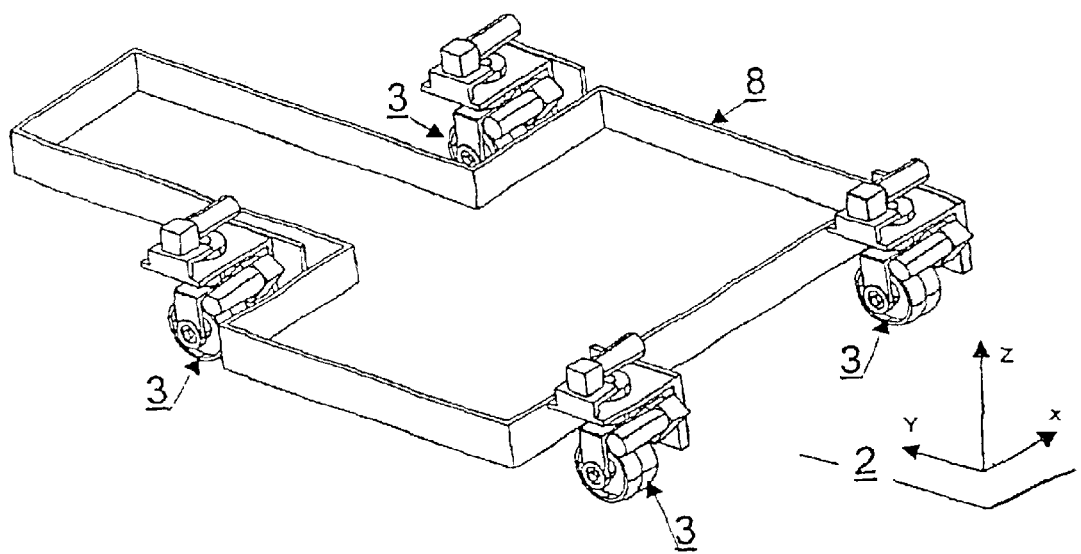
FIG. 1 is a perspective view of the device according to the invention in the form of a movable platform designed to support a medical X-ray apparatus.
Figure 1:
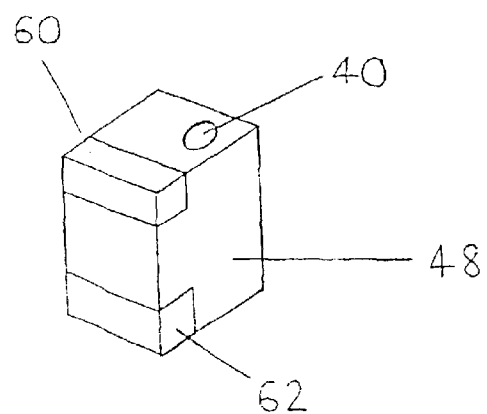
Figure 2:
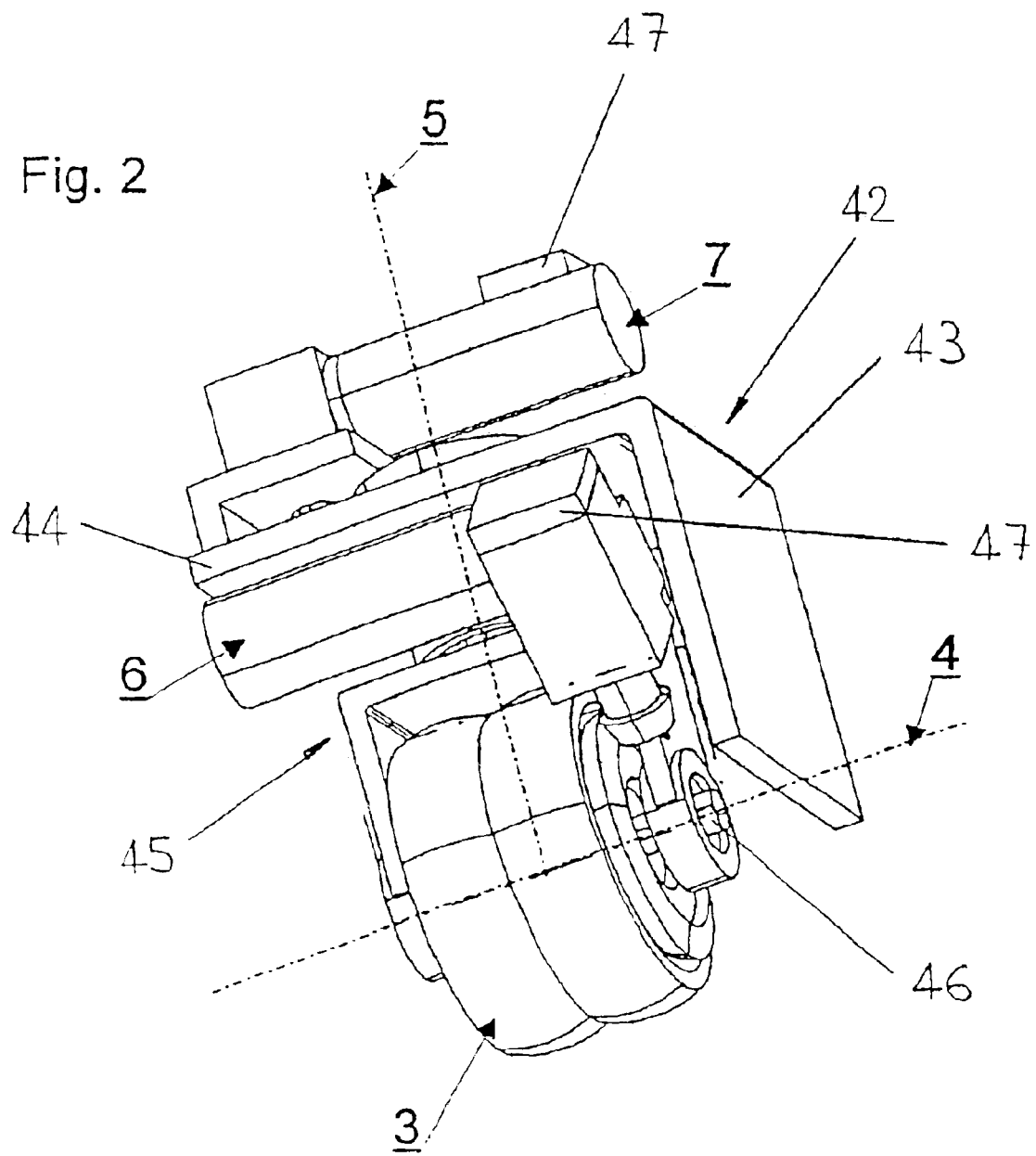
FIG. 2 is an enlarged perspective view of a roller of the device according to FIG. 1.

FIGS. 1 and 2 show the inventive device for moving a medical apparatus in a controlled manner in the two dimensions (x/y) of a plane 2 which is defined by the floor of an operating theatre. A plane frame 8 comprises four motor-driven rollers 3 provided with a first axis of rotation 4 extending parallel to said plane 2 and intersecting the centre of the roller 3 and a second axis of rotation 5 extending perpendicularly to said plane 2 and lying in the plane of the roller 3. The rollers 3 are mounted on the frame 8 by means of angle plates 42 the first plate portion 43 of which is fixed to the frame 8 while on the second plate portion 44, extending at a right angle to the first plate portion 43, the roller suspension 45 is fixed in such a way as to be rotatable about the second axis of rotation 5. The roller axles 46 are mounted on the roller suspension 45 concentrically to the axis of rotation 4 so that the rollers 3 fixed to said roller axles 46 are rotatable about the axis of rotation 4. The first drive devices 6 of the rollers 3, preferably realised as stepper motors, are connected to the second plate portions 44 on the inside of the angle plate 42, facing the rollers, and thus permit a rotation of the rollers 3 about their first axis of rotation 4. The second drive devices 7, preferably realised as stepper motors, are connected to the second plate portions 44 on the outside of the angle plates 42, facing away from the rollers 3, and permit a rotation of the roller suspensions 45 and, consequently, of the rollers 3 about their second axis of rotation 5. Both drive devices 6,7 are provided with receivers 47 which transmit the control signals emitted by a control device 48 to said drive devices 6,7. The control device 48 is preferably fixed programmable and subject to voice-controlled operation via a microphone 40. The voice signals received by the microphone 40 are converted into analogue signals or digital signals by a voice-coder or voice recognition unit 60 and transmitted to the control device 48. The control device 48 transforms the signals received from the voice recognition unit 60 into corresponding control signals intended for the drive devices 6;7 and radiotransmits these control signals by means of a transmitter 62 to the receivers 47 mounted on the drive devices 6;7. Instead of a single transmitter 62 which transmits the control signals to all the receivers 47, several transmitters may be used, each transmitter serving for the transmission of the control signals to a specially assigned receiver. The signal assignment may be realised, for example, by the use of specific frequencies. With new apparatuses there is preferably a possibility, instead of a radiotransmission of the control signals, to completely integrate the control device 48 into the device or the medical apparatus, so that a transmission of the control signals from the control device 48 to the drive devices 6;7 by means of cables is possible.

Figure 3:
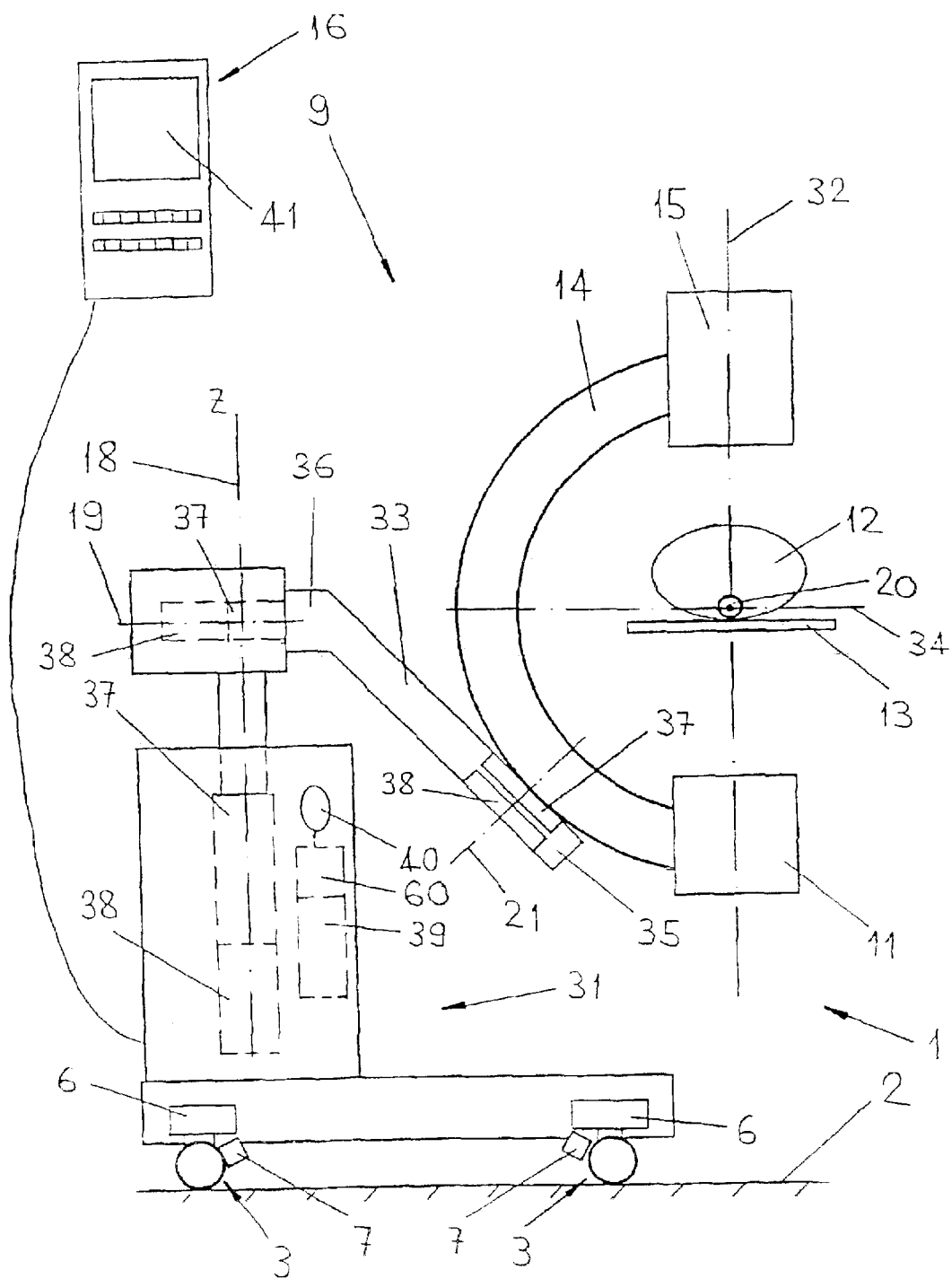
FIG. 3 is a view of the device as a whole, comprising the platform according to FIG. 1 and the medical X-ray apparatus put thereon.

FIG. 3 shows an embodiment of the inventive X-ray apparatus as a C-bow 9 having a pedestal 31 displaceable on the floor of the operating theatre, an X-ray source 11, and an X-ray receiver 15 arranged around an operating table 13 of an operating theatre. The displaceable pedestal 31 is freely movable in the plane 2 which is defined by the floor of the operating theatre by means of the controllable rollers 3 mounted on the pedestal 31 via their second axis of rotation 5, thus enabling a displaceability of the X-ray apparatus relative to two axes (x;y) extending perpendicularly to each other and lying in the plane 2. The X-ray source 11 and the X-ray receiver 15 are arranged in opposite positions on the central axis 32 and are fixedly connected by means of a support 14 shaped in the form of an arc of a circle. The central axis 32 extends perpendicularly to the image plane of the X-ray photograph to be taken and equally perpendicularly to the axis of symmetry 34 of the circular arc of the support 14. The support 14 of the C-bow 9 is displaceably connected to the first end piece 35 of another connecting support 33, the displaceability of said connecting support 33 relative to the C-shaped support 14 taking place along the outer periphery of the C-shaped support 14 thus enabling a rotation of the C-bow 9 about an axis 20 extending vertically to a plane defined by the axis of symmetry 34 and the central axis 32. In the special case represented by an isocentric design of the C-bow, the axis 20 lies in the centre of the semicircle defined by the support 14. This design presents numerous advantages, including the fact that an object once adjusted so as to be in the centre of the image will not leave the centre as the C-bow is rotated about the axis 20. This design is used in a new type of apparatus, such as the Siremobil Iso-C by Siemens. In the non-isocentric design, on the other hand, the axis 20 lies on the axis of symmetry 34 but outside the centre of the support 14, so that the distance between the axis 20 and the support 14 measured along the axis of symmetry 34 is longer than the radius of the support 14. Thus, the C-bow 9 is balanced, i.e. it does not have the tendency to automatically leave an adjusted projection as the C-bow 9 is rotated about the axis 20. The rotation of the C-bow 9 relative to the connecting support 33, equally provided only in connection with certain, specific designs, takes place about an axis 21 extending radially relative to the support 14 and intersecting the junction between the connecting support 33 and the support 14. With its second end piece 36, the connecting support 33 is movably connected to the displaceable pedestal 31. The mobility of the connecting support 33 relative to the displaceable pedestal 31 is realised, on the one hand, by its displaceability parallel to an axis 18 extending vertically to the plane 2 and by its rotation about said axis 18. On the other hand, the connecting support 33 may also be displaced parallel to a second axis 19 extending parallel to the plane 2, and the connecting support 33 may equally be rotated about said axis 19. The movable elements are driven by linear drive devices 37 and by rotational drive devices 6; 7; 38 which are controllable by means of a preferably electronic control device 39 integrated into the pedestal 31. The control device 39 is operated via voice control by means of a microphone 40 equally integrated into the pedestal 31. The control device 39 is preferably fixed programmable. Here again, the voice signals received by the microphone 40 are converted into analogue signals or digital signals by a voice-coder or voice recognition unit 60 and transmitted to the control device 39. The control device 39 transforms the signals received from the voice recognition unit 60 into corresponding control signals intended to be received by the drive devices 6; 7; 37; 38 and transmits these control signals. The control signals are transmitted from the control device 39 to the drive devices 6; 7; 37; 38 by means of cables. The X-ray photograph received by the X-ray receiver 15 is displayed on the screen 41 of an image intensifier 16. The drive devices 6; 7; 37; 38 are preferably realised as stepper motors.

Figure 4:
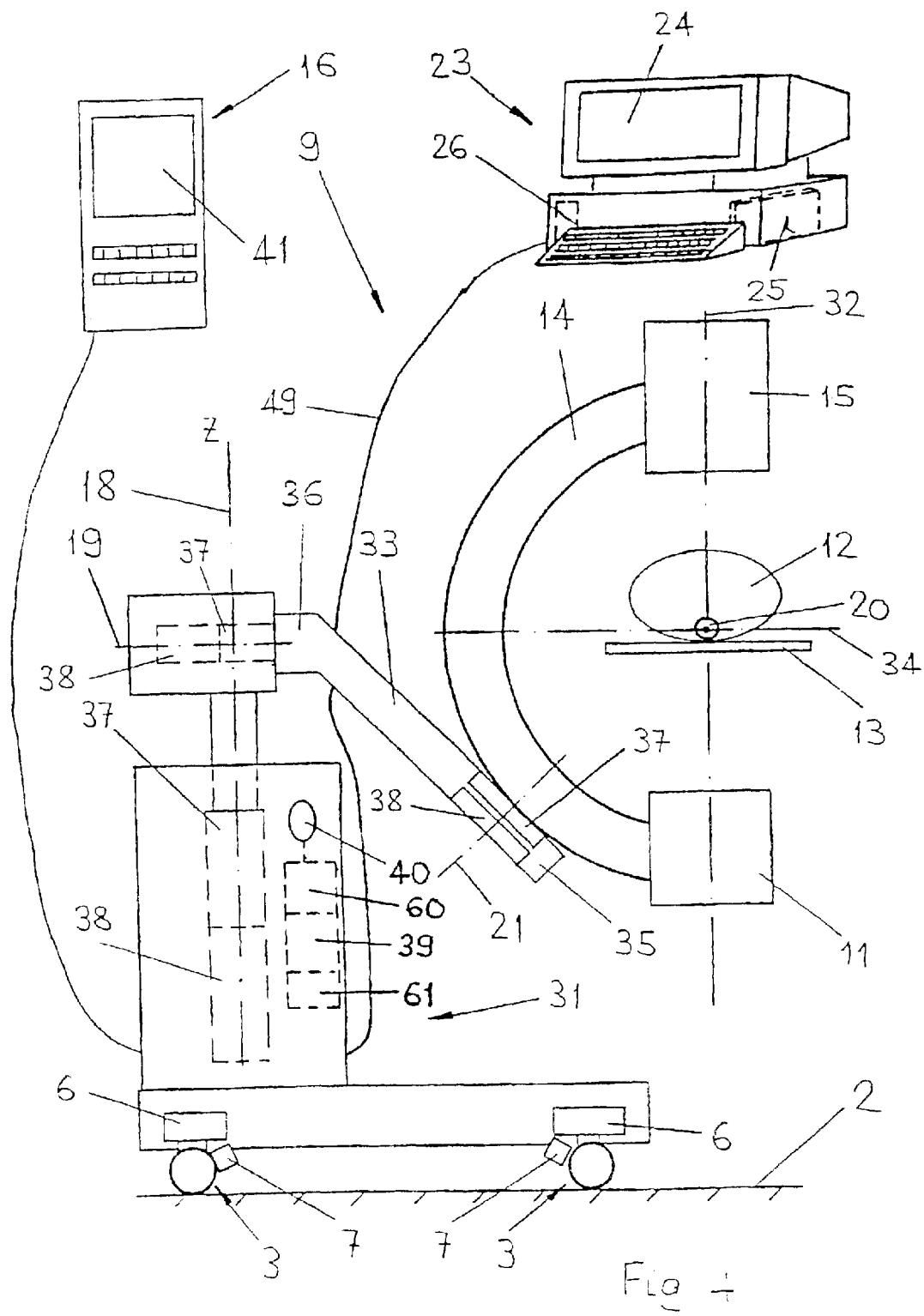
FIG. 4 shows a perspective view of the. computer-controlled device as a whole.

The embodiment of the inventive X-ray apparatus shown in FIG. 4 differs from the embodiment shown in FIG. 3 only in so far as the drive devices 6; 7; 37; 38 present on the pedestal 31 and on the connecting support 33 may, in addition, be controlled by an external computer 23. The control instructions may be entered via a keyboard 26 or a mouse (not shown). The storage of the positions and projections of the C-bow 9 takes place in the data memory 25 of the computer 23, so that these positions and projections are reproducible any number of times. The transmission of the control signals from the computer 23 to the drive devices 6; 7; 37; 38 is realised in this embodiment by means of a cable 49 by which the computer 23 is connected to the pedestal 31. In order to avoid the possibility of collisions with objects present in the operating theatre the projected path of displacement of the X-ray apparatus can previously be displayed on the display screen 24 of the computer 23. The computer 23 is connected to a preferably electronic control device 39 which, by analogy with the embodiment of the inventive X-ray apparatus described in FIG. 3, is integrated into the pedestal 31 and serves for controlling the movements of the linear drive devices 37 and the rotational drive devices 6; 7; 38. The control device 39 is operated either by data input into the computer 23 or via voice control by means of a microphone 40 equally integrated into the pedestal 31. The control device 39 is preferably fixed programmable. Here again, the voice signals received by the microphone 40 are converted into analogue signals or digital signals by a voice-coder or voice recognition unit 60 and transmitted to the control device 39. The control device 39 converts the signals received from the voice recognition unit 60 into corresponding control signals intended to be received by the drive devices 6; 7; 37; 38 and transmits these control signals. The control signals are transmitted from the control device 39 to the drive devices 6; 7; 37; 38 by means of cables. In this embodiment, the initial positioning of the C-bow 9 may be realised by data input into the computer 23 or by means of voice instructions addressed to the control device 39. With the aid of the computer 23, the position and projection occupied by the C-bow 9 is determined by calculating the lengths and the temporal succession of the displacements of all drive devices 6; 7; 37; 38 and stored in the data memory 25. Any position and projection occupied by the C-bow 9 and stored in this manner may subsequently be reproduced by activating a control function. This control function may be programmed in the control device 39 or in the computer 23 and may be activated by data input into the computer 23 or by voice instructions addressed to the control device 39. By activating this control function, the data defining the position and projection of the C-bow 9 which are stored in the data memory 25 are retrieved and transmitted to the control device 39, thus making it possible to restore the desired position and projection of the C-bow 9. According to a variant of the embodiment of the inventive X-ray apparatus described hereinabove, all drive devices 6; 7; 37; 38 may be controlled exclusively by the computer 23. It is also possible to have the control device 39 plus the voice recognition unit 60 completely integrated with the computer 23.

Figure 5:
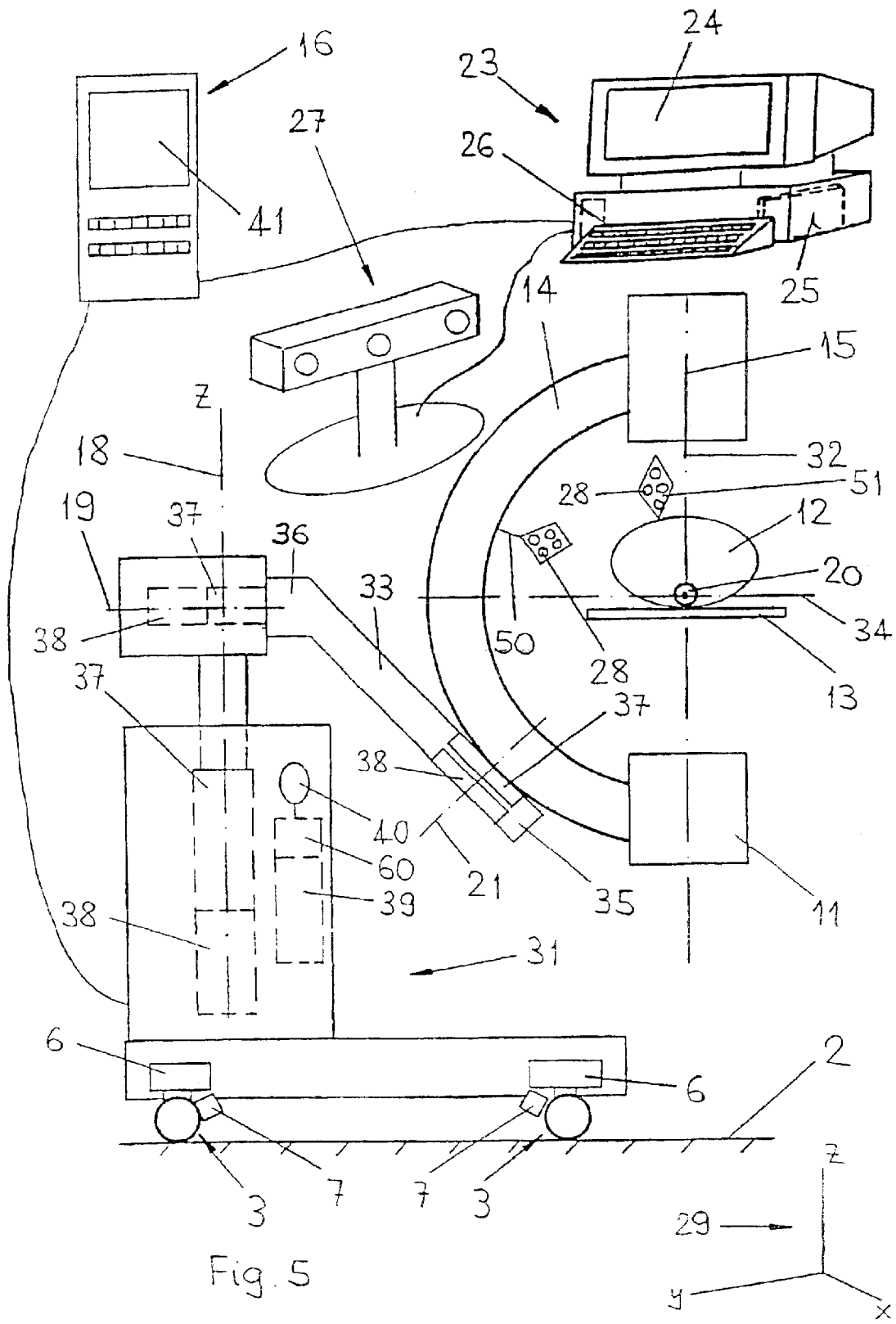
FIG. 5 is a perspective view of a device as a whole provided with a position detector.

FIG. 5 shows the embodiment of the X-ray apparatus according to the invention combined with a surgical navigation system. This embodiment differs from the embodiment shown in FIG. 4 only in so far as the C-bow 9 is provided with a reference base 50. A further reference base 51 is applied to the patient 12. The reference bases 50;51 comprise each four optical markers 28 arranged in a non-collinear manner and realised in the form of LEDs. The surgical navigation system comprises an optoelectronic position detector 27 by means of which the positions of the markers 28 are detectable and the coordinates defining the location of the markers 28 relative to a three-dimensional coordinate system 29 extending throughout the operating theatre are storable in the data memory 25. Thus, it is possible to use the computer 23 in order to detect changes in the position of a patient 12. The stored positions and projections of the C-bow 9 are transformed by the computer 23 in such a way that while the patient 12 occupies the modified, second position, a position and projection of the C-bow is calculated (and the C-bow is moved to said position and projection) which makes it possible to take an X-ray photograph in a projection plane corresponding to that of an X-ray photograph taken previously while the patient 12 had occupied the first position.

What is claimed is:

1. The device for moving a medical apparatus (1), in particular an X-ray apparatus, in a controlled manner in the two dimensions (x/y) of a plane (2), especially a plane extending parallel to the floor of an operating theatre, by means of at least three motor-driven rollers (3) which are provided with a first axis of rotation (4) extending parallel to said plane (2) and intersecting the center of the roller (3), and with a second axis of rotation (5) extending perpendicularly to said plane (2) and lying in the plane of the roller (3) or parallel thereto, the rollers (3) being positioned in a fixed relationship relative to one another, whereby A) each of the rollers (3) is provided with a first drive device (6) by means of which the roller (3) is rotatable about the first axis of rotation (4); and B) each of the rollers (3) is provided with a second drive device (7) by means of which the roller (3) is rotatable about the second axis of rotation (5) so as to change its direction of travel, and the device C) comprises a control device (39) by means of which control instructions entered by the operator are convertible into corresponding control signals for the first and second drive devices (6;7), and wherein D) the device comprises a microphone (40) and a voice recognition unit (60) making it possible to operate the control unit (39) via voice control.

2. The device as claimed in claim 1, wherein the rollers (3) are fixed directly to the medical apparatus (1) via their second axis of rotation (5).

3. The device as claimed in claim 1, wherein, via their second axis of rotation (5), the rollers (3) are fixed to a frame (8) that is designed to serve as a platform for the medical apparatus (1).

4. The device as claimed in claim 1, wherein the first and second drive devices (6;7) are electronically controllable stepper motors.

5. The device as claimed in claim 1, wherein the medical apparatus (1) is an X-ray apparatus, which comprises a pedestal (31) to which the rollers (3), each having a first and second drive device (6;7) for the movement of the device (1) in the plane (2), are attached.

6. The device as claimed in claim 5, further comprising:

A) a C-bow (9) being capable of translatory and rotational movement relative to the pedestal (31) in the axial directions x, y, z of the coordinate system (29), said C-bow including an X-ray source (22) and an X-ray receiver (15) that are arranged and fixedly connected in opposite positions on a central axis (32) by means of a support (14) of a C-bow, the central axis extending vertically to the image plane of the X-ray photograph to be taken;

B) drive devices (37;38) mounted on the pedestal (31) for moving the C-bow (9) relative to the pedestal (31); and C) a control device (39) for converting operator-entered control instructions, which concern a particular position and projection to be occupied by the C-bow (9), into corresponding control signals to be transmitted to the drive devices (6;7;37;38).

7. The device as claimed in claim 6, further comprising a connecting support (33) having a first end piece (35) and, longitudinally opposite thereto, a second end piece (36) and wherein the first end piece (35) is movably connected to the C-bow (9) while the second end piece (36) is movably connected to the pedestal (31).

8. The device as claimed in claim 7, wherein the pedestal (31) is provided with drive devices (37;38) permitting a displacement of the connecting support (33) relative to the pedestal (31) and wherein the connecting support (33) is provided with at least one drive device (37) permitting displacement of the C-bow (9) relative to the connecting support (33).

9. The device as claimed in claim 7, wherein the outer periphery of the support (14) is connected to the first end piece (35) by a slide bearing so as to be tangentially slidable.

10. The device as claimed in claim 7, wherein the second end piece (36) is connected to the pedestal (31) so as to be displaceable along and rotatable about an axis (18) extending vertically to the plane (2) and about an axis (19) extending vertically to the axis (18).

11. The device as claimed in claim 6, further comprising a hand-operated control console for manipulating the control device (39).

12. The device as claimed in claim 6, further comprising a microphone (40) and a voice recognition unit (60) to permit operation of the control unit (39) via voice control.

13. The device as claimed in claim 6, further comprising a computer (23) including at least a data memory (25), a display screen (24), and a keyboard (26).

14. The device as claimed in claim 13, wherein the drive devices (6;7;37;38) are automatically controllable by the computer (23) in response to data input into said computer and that the C-bow may thus be displaced in a controlled manner by an operating surgeon by entering data into the computer (23).

15. The device as claimed in claim 13, wherein the position and orientation of the C-bow (9) is stored in the data memory (25) of the computer (23).

16. The device as claimed in claim 15, wherein a control function is stored in the data memory (25) and the control function is operable to displace the C-bow (9) so as to reproduce any given position and orientation of the C-bow (9) stored in the data memory (25) of the computer (23).

17. The device as claimed in claim 16, wherein the computer (23) is connected to the control device (39) and the activation of the control function is realized by use of a control console manipulated by the operating surgeon.

18. The device as claimed in claim 16, wherein the computer (23) is connected to the control device (39) and the activation of the control function is realized by means of voice control.

19. The device as claimed in claim 6, in combination with a surgical navigation system that comprises an optoelectronic position detector (27).

20. The device as claimed in claim 19, wherein at least three optical markers (28), which are arranged in a non-collinear manner, are fixed to the C-bow (9), and wherein positions of the markers (28) are determined by the optoelectronic position detector (27) and coordinates of the markers positions relative to a three-dimensional coordinate system (29) extending throughout the operating theatre are stored in the data memory (25).

21. The device as claimed in claim 19, further comprising at least one reference base (51) to be applied to a patient (12), said at least one reference base including at least three optical markers (28) arranged in a non-collinear manner, so that a position of the markers (28) may be determined by the optoelectronic position detector (27) and position coordinates of the markers (28) relative to a three-dimensional coordinate system (29) extending throughout the operating theatre may be stored in the data memory (25).

22. The device as claimed in claim 6, wherein the drive devices (37, 38) are linear stepper motors.

23. The device as claimed in claim 22, wherein the stepper motors are digitally controlled.

24. A method for moving an X-ray apparatus, in a controlled manner by means of a device according to claim 1, comprising the steps of:
   A) inputting an instruction to move the apparatus to a desired position;
   B) using a control device (39, 48) to transform the input instruction into control signals;
   C) transmitting the control signals to drive devices (6;7;37;38) mounted on said device; and,
   D) operating the drive devices (6; 7; 37; 38) and thereby displacing the movable elements to the desired position.

25. The method as claimed in claim 24, wherein the instruction-inputting step is realized by use of a hand-operated control console.

26. The method as claimed in claim 24, wherein the instruction-inputting step is realized as a voice-controlled instruction input.

27. The method as claimed in claim 24, wherein the instruction-inputting step is realized as an input into a computer (23) by means of a keyboard (26) or a mouse.

28. The method as claimed in claim 24, wherein any given position once occupied by the apparatus may be stored in the data memory (25) of a computer (23).

29. The method as claimed in claim 28, wherein the position of the apparatus is calculated in the computer (23) by determining a length and a temporal succession of the displacements of the movable elements and wherein data on the position thus obtained is subsequently stored in the data memory (25).

* * * * *